United States Patent
Bolduc et al.

[11] Patent Number: 5,824,008
[45] Date of Patent: Oct. 20, 1998

[54] SYSTEM FOR APPLYING FASTENERS TO TISSUE

[75] Inventors: Lee Bolduc, Mountain View; Thomas A. Kramer, San Carlos; Brian A. Hodges, Foster City; Tim McCoy; John Lunsford, both of San Carlos, all of Calif.

[73] Assignee: Origin Medsystems, Inc., Menlo Park, Calif.

[21] Appl. No.: 812,959

[22] Filed: Mar. 5, 1997

Related U.S. Application Data

[60] Continuation of Ser. No. 499,279, Jul. 7, 1995, which is a division of Ser. No. 286,878, Aug. 5, 1994, Pat. No. 5,582,616.

[51] Int. Cl.⁶ .................................................. A61B 17/00
[52] U.S. Cl. ........................ 606/43; 606/139; 606/213; 227/901
[58] Field of Search ................................. 606/140–143, 606/139, 151, 148, 213; 227/175.1–182, 901, 19

[56] References Cited

U.S. PATENT DOCUMENTS

| | | | |
|---|---|---|---|
| 2,391,792 | 12/1945 | Miles et al. | 108/33 |
| 3,858,783 | 1/1975 | Kapitanov et al. | 227/108 |
| 3,870,048 | 3/1975 | Yoon . | |
| 4,204,541 | 5/1980 | Kapitanov . | |
| 4,595,007 | 6/1986 | Mericle . | |
| 4,627,437 | 12/1986 | Bedi et al. . | |
| 4,976,715 | 12/1990 | Bays et al. | 606/77 |
| 5,007,921 | 4/1991 | Brown | 606/21 |
| 5,053,047 | 10/1991 | Yoon | 606/223 |
| 5,163,343 | 11/1992 | Gish | 81/120 |
| 5,171,247 | 12/1992 | Hughett et al. | 606/142 |
| 5,192,288 | 3/1993 | Thompson et al. | 606/139 |
| 5,217,486 | 6/1993 | Rice et al. | 606/220 |
| 5,222,976 | 6/1993 | Yoon | 606/223 |
| 5,242,457 | 9/1993 | Akopov et al. | 606/144 |
| 5,258,000 | 11/1993 | Gianturco | 606/213 |
| 5,269,792 | 12/1993 | Kovac et al. | 606/158 |
| 5,282,807 | 2/1994 | Knoepfler | 606/143 |
| 5,297,714 | 3/1994 | Kramer | 606/219 |
| 5,320,630 | 6/1994 | Ahmed | 606/140 |
| 5,330,503 | 7/1994 | Yoon | 606/223 |
| 5,356,064 | 10/1994 | Green et al. | 227/177 |
| 5,356,424 | 10/1994 | Buzerak et al. | 606/23 |
| 5,411,522 | 5/1995 | Trott | 606/232 |
| 5,437,266 | 8/1995 | McPherson et al. | 600/217 |
| 5,499,990 | 3/1996 | Schülken et al. | 606/144 |
| 5,500,001 | 3/1996 | Trott | 606/232 |
| 5,501,683 | 3/1996 | Trott | 606/72 |
| 5,626,613 | 5/1997 | Schmieding | 606/75 |
| 5,662,683 | 9/1997 | Kay | 606/232 |

FOREIGN PATENT DOCUMENTS

| | | |
|---|---|---|
| A-20325/95 | 5/1995 | Australia . |
| 1006874A6 | 1/1995 | Belgium . |
| 554 653 A2 | 1/1993 | European Pat. Off. . |
| 645 149 A1 | 9/1994 | European Pat. Off. . |
| 648 471 A1 | 10/1994 | European Pat. Off. . |
| 663 184 A1 | 1/1995 | European Pat. Off. . |
| 686 373 A1 | 6/1995 | European Pat. Off. . |
| 663184 A1 | 7/1995 | European Pat. Off. . |
| 320.731 | 4/1902 | France . |
| 2299548 | 8/1976 | France . |
| 295962 | 5/1916 | Germany . |
| 2 148 232 | 10/1983 | United Kingdom . |

*Primary Examiner*—Jeffrey A. Schmidt
*Attorney, Agent, or Firm*—Fulwider, Patton, Lee & Utecht, LLP

[57] ABSTRACT

A helical fastener having a high retentive surface area is provided and has a first end for enhancing penetration into tissue and a second end comprising a coil sectioning a diameter of the fastener for receiving longitudinal and rotational forces. The helical fasteners are attached to body tissue by a fastener applicator having a proximal portion comprising a handle and an actuator and an elongate distal portion for housing a plurality of fasteners. A transferring action of the actuator provides longitudinal and rotational movement of the fasteners out of the distal portion and into body tissue.

9 Claims, 8 Drawing Sheets

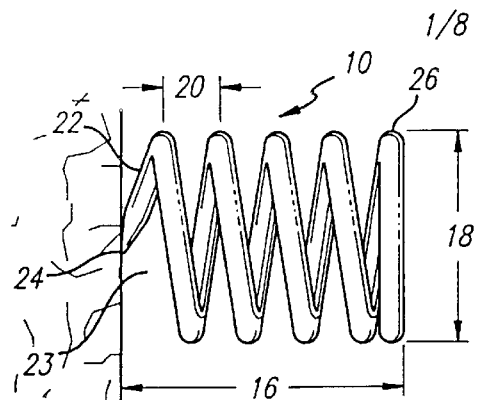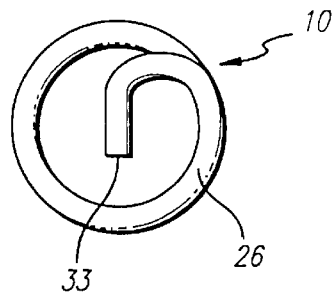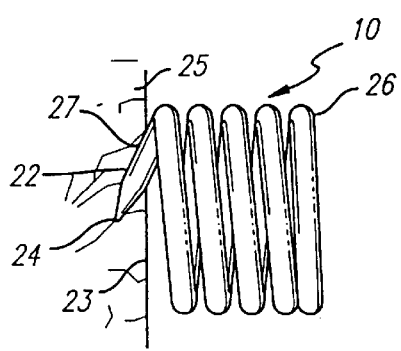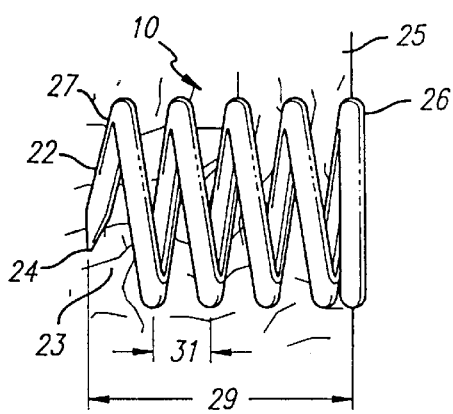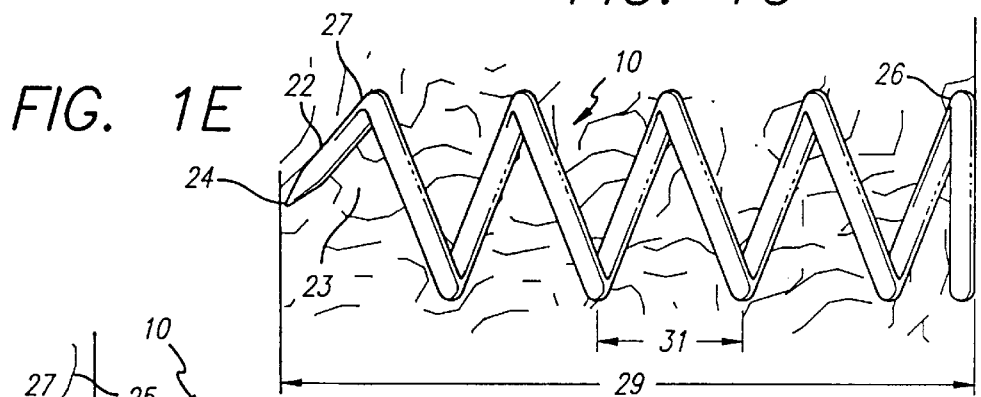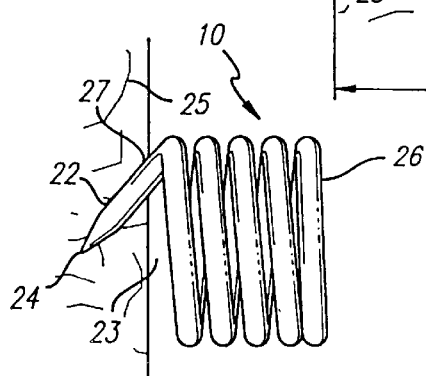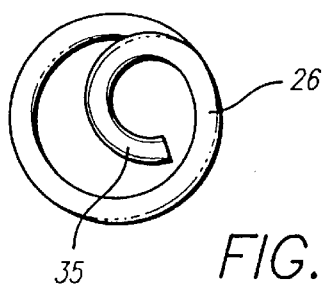

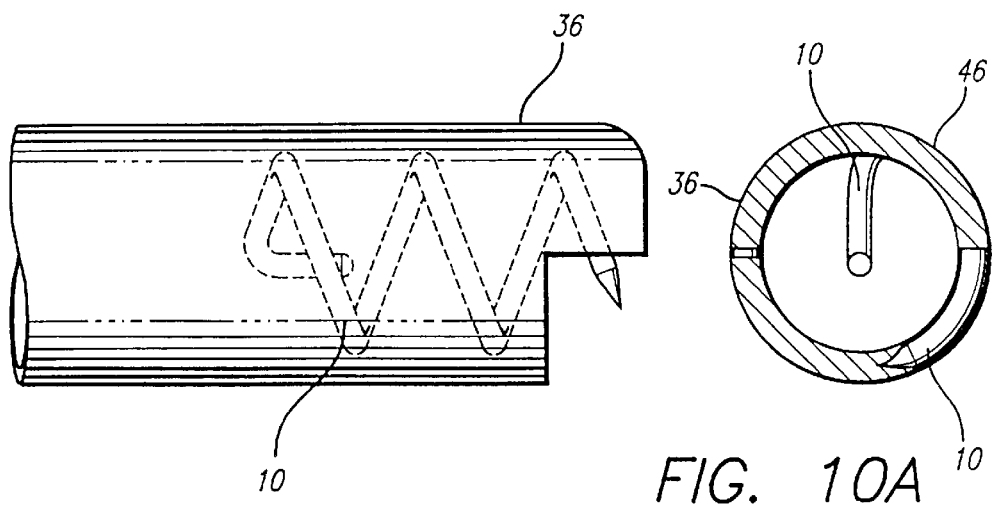
FIG. 10
FIG. 10A
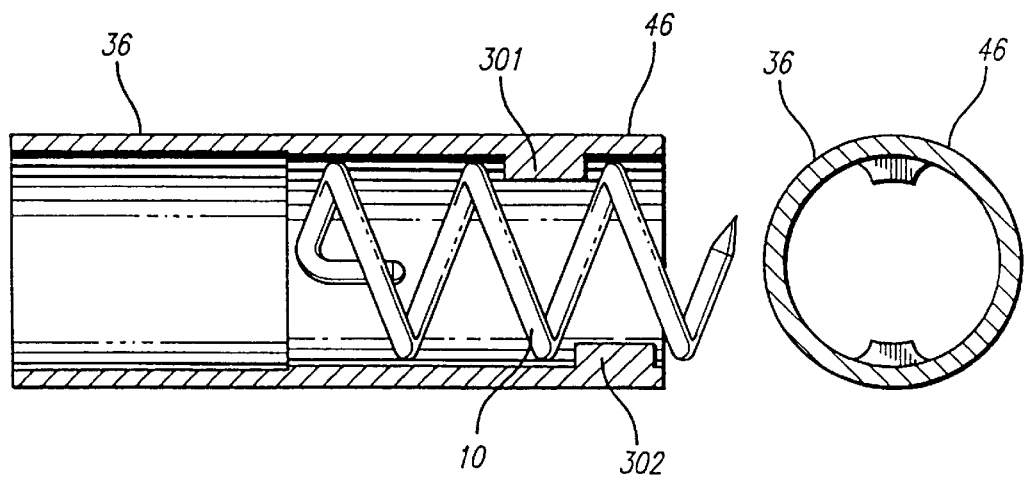
FIG. 11
FIG. 11A

SYSTEM FOR APPLYING FASTENERS TO TISSUE

This is a continuation of application Ser. No. 08/499,279, filed on Jul. 7, 1995 is pending, which is a divisional of application Ser. No. 08/286,878, filed on Aug. 5, 1994, now U.S. Pat. No. 5,582,616.

BACKGROUND OF THE INVENTION

This invention relates to surgical fasteners and their associated applicators, and more particularly, surgically fastening material to tissue.

Fasteners have been used surgically to eliminate the need for suturing, which is both time consuming and inconvenient. In many applications the surgeon can use a stapler apparatus, i.e., a fastener implanting device loaded with surgical fasteners to accomplish in a few seconds what would have taken many minutes to perform by suturing. This reduces blood loss and trauma to the patient.

Conventional surgical fasteners have been in the form of ordinary metal staples, which are bent by the delivery apparatus to hook together body tissue. Typically, conventional staples comprise a pair of legs joined together at one end by a crown. The crown may be a straight member connecting the legs or may form an apex. Moreover, the legs may extend substantially perpendicular from the crown or at some angle therefrom. Irrespective of the particular configuration, however, conventional staples are designed so that they may be deformed to hold body tissue.

Accordingly, the stapler applicators have conventionally embodied structure functioning to project the conventional staple into tissue as well as to deform the staple so that it is retained against the tissue. Generally speaking, typical applicators include an anvil cooperating with means to eject the conventional staple from the applicator. In some applications, access to the body tissue from two opposite directions is available and the anvil can operate to deform the legs of the staple after they have passed through the body tissue. In applications where access to the tissue is from only one direction, the anvil may deform the crown of the conventional staple so that its legs will project into the body tissue in a fashion so as to hold the staple against the tissue.

Since conventional staples require deformation and must cooperate with applicators having an anvil or other means to deform the staples, conventional applicators typically comprise complex structures and can be prohibitively expensive. Conventional applicators must embody structure functioning to not only eject the fasteners but to do so in a manner so that the fastener deforms properly and timely.

In some applications, conventional applicators must be equipped with structure functioning to move the anvil into and out of position so that when the fastener is ejected from the applicator, the anvil is properly positioned and once fastener deformation is complete, moves out of position, thereby allowing the process to be repeated. Moreover, the anvil must be formed into a proper configuration so that fastener deformation can be repeated accurately. Further, the force between the fastener and the anvil must be controlled so that repeated deformation is accomplished. The objectives of many inventions in this field have been to accomplish these goals by the simple manipulation of a single lever. It is to be appreciated, therefore, that the fastener applicators have become complex and expensive instruments.

Two part fasteners have also been conventionally utilized, where a barbed staple is used in conjunction with a retaining piece to hold the staple in place. Typically, the two part staple comprises a crown or backspan and two barbed prongs which are engaged and locked into a separate retainer piece. In use, the staple is pressed into the body tissue so that the barbs penetrate the tissue and emerge from the other side where they are then locked into the retainer piece. Retainers prevent the staple from working loose from the tissue. The two piece fasteners cannot be unlocked and are not removable.

Like other conventional applications, however, the two piece fasteners require the staple delivery apparatus to have access to both sides of the tissue. Thus, as with the other conventional applications, two piece fasteners are limited since they cannot be used where access to tissue is from one direction only.

In those situations where access to body tissues is limited to one direction, as in grafting procedures, deformable surgical fasteners have been conventionally employed. As mentioned previously, however, the applicators commonly used in these situations embody an anvil cooperating with a fastener to deform it and consequently, tend to be of a complex design.

Some advancements have been made in this area so that applicators functioning to attach grafts to tissue, for instance, are not required to embody an anvil and may, therefore, have a more simple design. In particular, it has been suggested in the art to employ fasteners with barbs, thereby eliminating the need for deforming the fastener. These fasteners are limited, however, since the path created in the graft and tissue by the barbs as the fastener is pressed into the graft and tissue may allow the fastener to loosen its grip or to entirely back out of engagement. Moreover, due to their sole reliance upon barbs to retain tissue, the barb fasteners are further limited in that they may not have a great enough retentive surface area for securely holding tissue in place.

To circumvent or overcome the problems and limitations associated with conventional fasteners and applicators, a simple applicator that dispenses a surgical fastener having high surface area for retentive contact with tissue and that can be delivered into body tissue from one direction may be employed. The present invention embodies these characteristics.

SUMMARY OF THE INVENTION

The invention includes a surgical fastener and an applicator used in delivering the fastener into body tissue. The fastener and applicator of the present invention may be used in a number of medical procedures including ligating tissue, hernia mesh repair, bladder neck suspension, and in conjunction with implant drug delivery systems or procedures involving positioning of surgical or implantable devices in a patient's body.

The preferred embodiment of the surgical fastener of the present invention is formed into the configuration of a continuous helical coil. The continuous helical coil is longitudinally collapsible and expandable. At the distal end of the helical fastener is a point for enhancing penetration into tissue. The proximal end of the helical fastener has a T-bar which sections the diameter of the fastener, thereby providing a surface for receiving and transmitting longitudinal and rotational forces so that the fastener may be driven into tissue by a corkscrew action. The pitch and length of the helical fastener may vary upon the application as can its diameter and configuration of the most proximal and distal coils comprising the fastener. Additionally, the material selection and fastener stiffness may be selected with a particular application in mind.

In another embodiment of the surgical fastener, the fastener comprises a double continuous helical coil that is also longitudinally collapsible and expandable and may embody various configurations depending upon the application. Moreover, the distal end of the double helical fastener comprises two points for enhancing penetration into tissue and its proximal end comprises a connector bar which connects the two helixes as well as sections the diameter of the double helical fastener. In yet another embodiment, the surgical fastener further comprises a pivot post extending through the center of the fastener and operating to provide the fastener with a stable pivot. In any of the embodiments, one or more barbs may be employed near the point to enhance anchoring characteristics.

A preferred embodiment of the fastener applicator of the present invention includes a proximal portion and a distal portion. The proximal portion is preferably fabricated to be a "reusable" component and the distal portion a "disposable" component. Alternatively, both the distal and proximal portion can be made disposable. The distal portion is elongate and embodies an outer tube housing an inner rotator, a lock clip/indicator and a load spring. The proximal portion includes a handle. In the preferred embodiment of the distal portion, a thread form comprising an interlock spring is provided within the outer tube. The rotator includes a structure running longitudinally along its length that functions to receive the T-bar or connector bar of the fastener and in this way, the rotator may hold a plurality of fasteners. The load spring applies a force against the lock clip/indicator operating to bias the plurality of springs distally within the outer tube and towards the nose piece. The thread form functions to engage the coils of the helical fasteners and when rotating the rotator, a fastener is driven from the distal end of the applicator. In other embodiments of the applicator, the distal end has various other structures functioning to engage the coils of the fastener and to drive them from the distal end of the applicator. In one other embodiment, the distal end comprises a nose piece protrusion for engaging the fastener.

In order to cause the rotator to rotate, the proximal portion of the applicator has a handle and an actuator cooperating with the rotator. In a preferred embodiment, the proximal portion of the applicator embodies a lever pivotally attached about a midpoint to the handle. A first end of the lever is configured to be gripped by hand and a second end is adapted to engage a nut driver. The nut driver travels along a helical lead screw which is connected to the rotator. When the lever is squeezed by hand the nut driver travels along the lead screw causing it to rotate, and through the connection of the lead screw to the rotator, the action of the lead screw causes the rotator to rotate.

Further, the lever comprises a midsection extension. Pivotally attached to the midsection extension of the lever is a spring loaded pawl adapted to releasably engage gear teeth formed in the interior of the handle. The spring loaded pawl prohibits the lever from backstroking until it has been completely depressed. Upon complete depression of the lever, the pawl clears the gear teeth and the spring, biasing the pawl, rotates the pawl away from the teeth, thereby allowing the lever to return to its undepressed condition.

In another embodiment of the proximal portion of the applicator, the lever is pivotally attached at a first end to the handle, the second end being adapted to engage the nut driver. Further, rather than embodying a spring loaded pawl, this alternate embodiment of the proximal portion includes a clutch assembly or releasable connection between the lead screw and rotator and cooperating means to prohibit the lever from backstroking until it has been completely depressed.

Other features and advantages of the present invention will become apparent from the following detailed description, taken in conjunction with the accompanying drawings, which illustrate, by way of example, the principals of the invention.

BRIEF DESCRIPTION OF THE DRAWINGS

FIG. 1 depicts a perspective view of a fastener of the present invention, illustrating a side view of a helical fastener.

FIG. 1A depicts another perspective view of the fastener of the present invention, illustrating an end view of the helical fastener.

FIG. 1B depicts a schematic view of a fastener of the present invention, illustrating a substantially collapsed helical fastener with a relatively small gap that has been partially inserted into tissue.

FIG. 1C depicts a schematic view of a fastener of the present invention, illustrating the helical fastener depicted in FIG. 1B completely inserted into tissue.

FIG. 1D depicts a schematic view of a fastener of the present invention, illustrating a substantially collapsed helical fastener with a relatively large gap that has been partially inserted into the tissue.

FIG. 1E depicts a schematic view of a fastener of the present invention, illustrating the helical fastener depicted in FIG. 1D completely inserted into tissue.

FIG. 1F depicts a perspective view of another embodiment of the present invention, illustrating an end view of the helical fastener.

FIG. 10 is a schematic cross-sectional view of the terminal end of the applicator, illustrating still yet another embodiment of the terminal end.

FIG. 10A is a schematic cross-sectional end view of the embodiment of the terminal end of the applicator shown in FIG. 10.

FIG. 11 is a schematic cross-sectional view of the terminal end of the applicator, illustrating another embodiment of the terminal end.

FIG. 11A is a schematic cross-sectional end view of the embodiment of the terminal end of the applicator shown in FIG. 11.

DETAILED DESCRIPTION OF THE PREFERRED EMBODIMENTS

Figures 2, 2A, 2B:
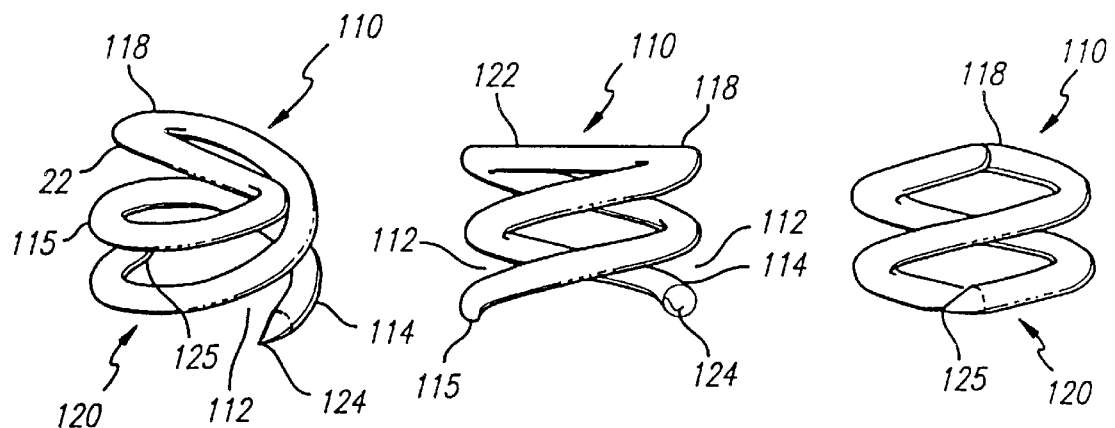
FIG. 2 depicts a perspective view of another embodiment of the present invention, illustrating a double helical fastener.
FIG. 2A is a front view of the double helical fastener of FIG. 2.
FIG. 2B is side view of the double helical fastener of FIG. 2.

As is shown in the drawings, which are included for purposes of illustration and not by way of limitation, the invention is embodied in a continuous helical fastener and an applicator therefor. The helical fastener has a high retentive surface area and the applicator has a simple design and functions to dispense the helical fasteners, without substantially deforming the fasteners, into body tissue, access to which is from one direction only. Some conventional fasteners require deformation to hold tissue and are consequently limited since they require complex applicators to attach them into tissue. Other conventional fasteners lack high retentive surface area for securely holding tissue. Still other fastener/applicator systems require access to tissue from two directions in order to accomplish attaching a fastener to tissue. Thus, the helical fastener and applicator of the present invention provides a superior means to attach fasteners to tissue.

Figure 5:
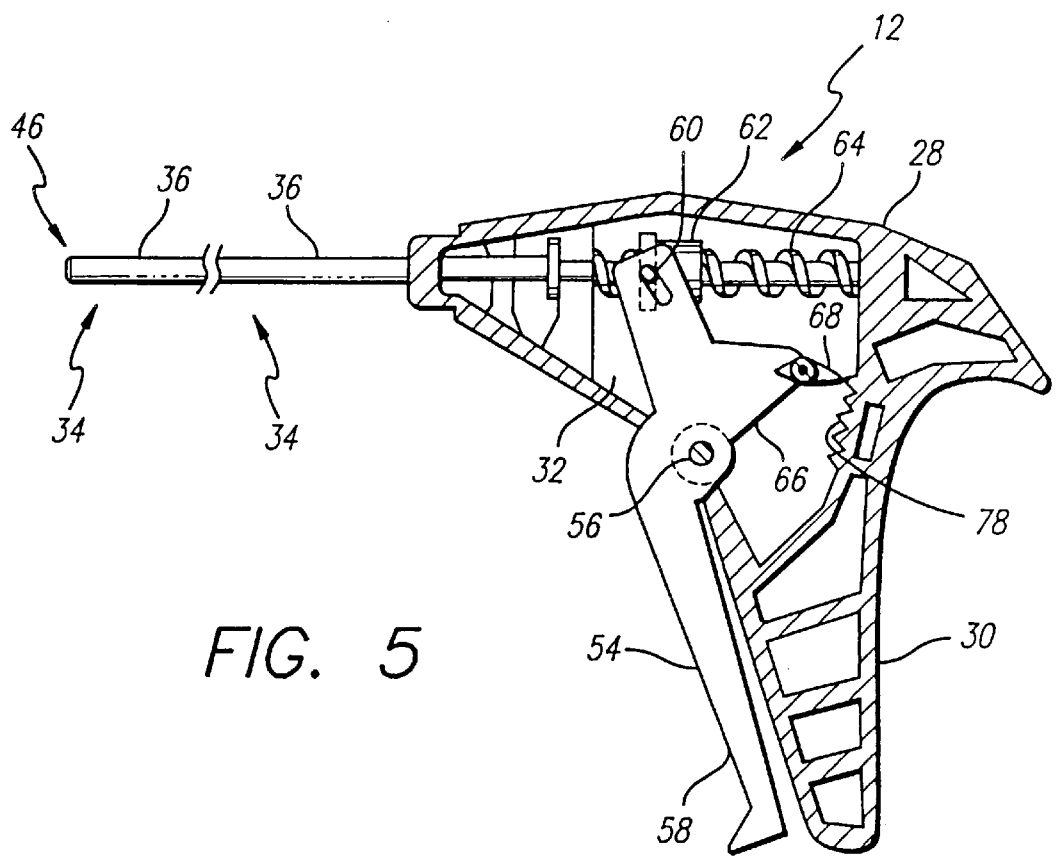
FIG. 5 depicts a schematic cross-sectional view of an applicator of the present invention, illustrating a side view of the applicator.

One embodiment of the present invention (FIGS. 1, 1A and 5) is embodied in a helical fastener 10 which is attached to tissue by employing a novel applicator 12 which rotates the fastener 10 into tissue. The dimensions and physical characteristics of the helical fastener 10 are selected to insure a secure attachment of the fastener 10 to tissue. Similarly, the dimensions and physical characteristics of the applicator 12 utilized to dispense the fasteners 10 into tissue are dependent upon the application.

In a preferred embodiment, the fastener 10 is formed into the configuration of a continuous helix and may have a depth 16, a diameter 18 and a pitch 20 determined by the application. The continuous helix may be longitudinally collapsible and expandable. The cross-sectional profile of the continuous helix is substantially circular in the preferred embodiment but can be square, rectangular or triangular. In a particular application such as mesh anchoring for hernia repair, the pre-formed pitch can be 0.050 inches. However, the pre-formed pitch can vary from 0 to a maximum of approximately 3.0 times the coil diameter. In other embodiments, it is contemplated that the pitch 20 vary along the length of the fastener 10 so as to optimize the retaining force of the fastener 10. Moreover, since the continuous helical coil is preferably longitudinally collapsible and expandable, upon insertion into tissue, the final pitch 31 may be less than or greater than the pre-formed pitch. If the coil is made of rigid construction, as is also contemplated, pitch would be made substantially fixed. The diameter in the preferred embodiment may be 5 mm; however, designs ranging from 1 mm and up are contemplated. In practice, the depth 16 of the fastener 10 must be selected so that the extent of fastener penetration into tissue is sufficient to hold the fastener 10 in place.

Moreover, distal end 22 of the fastener 10 is to be configured such that a gap 23 exists between the most distal coil 27 (or first coil) of the fastener 10 and its adjacent coil. As may be appreciated from the preferred embodiment of FIGS. 1B through 1E, as the fastener 10 is pressed against tissue 25, all of the coils substantially collapse except the most distal coil 27, leaving the gap 23 to determine the path the fastener 10 takes as it is rotated into the tissue 25 and more importantly, the extent of penetration 29 into the tissue 25 and final pitch 31 of the fastener 10 in tissue. Although FIG. 1B shows substantially all of the coils being collapsed, it is to be appreciated that, depending upon the applicator utilized to implant the fastener 10, fewer coils than all of the coils may be collapsed at any one time. It remains, however, that since the fastener 10 is longitudinally collapsible and expandable, it is the gap 23 that generally determines final pitch 31. Accordingly, the magnitude of the gap 23 can be varied, depending upon the application, to achieve the desired final pitch 31 and penetration 29 in tissue. Thus, the greater the gap 23, upon insertion of the fastener 10 in tissue, the greater the penetration 29 and final pitch 31 of the fastener 10 in tissue.

In the preferred embodiment, the distal end 22 of the helical fastener 10 terminates with a point 24. The point 24 may be sharp or blunt depending upon the tissue to which the fastener 10 will be affixed. Additionally, one or more barbs or a sharp point projecting in reverse direction to point 24 (not shown) can be added to fastener 10 near point 24 to enhance anchoring characteristics of the fastener. A proximal end 26 of the helical fastener 10 may comprise structure functioning to receive and transmit applied longitudinal forces. In the preferred embodiment, the most proximal coil is formed into a T-bar 33 that perpendicularly sections the diameter 18 of the fastener 10. In alternate embodiments, it is also contemplated that the most proximal coil section the diameter 18 non-perpendicularly or be formed into a spiral 35 existing in a single plane (See FIG. 1F).

Concerning the material of the helical fastener 10, it is contemplated in the preferred embodiment that the fastener be made from semi-stiff implantable wire, such as titanium, wound into a helical shape. In alternate embodiments, the helical fastener 10 may comprise plastic or absorbable materials. Examples of materials that can be used in constructing the helical fastener 10 include titanium, titanium alloys, stainless steel, nickel, chrome alloys and any other biocompatible implantable metals. Other options for materials are liquid crystal polymers, HDPE, polyglycolic acid, and polyglycolid hydroxgacetic acid. Further, it may also be desirable to coat the fastener, or a portion thereof, with a biocompatible lubricious material that provides for easier delivery of the fastener into tissue.

Figures 2C, 3, 3A:
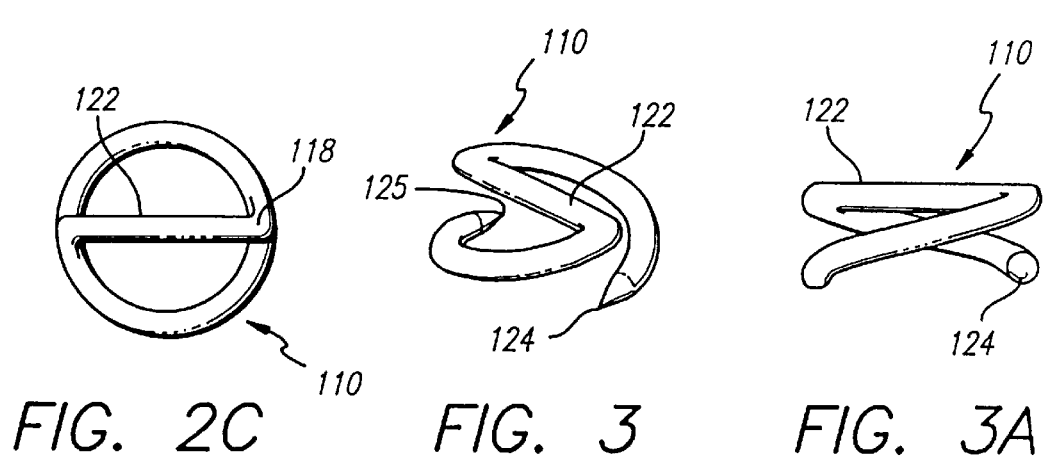
FIG. 2C is a top view of the double helical fastener of FIG. 2.
FIG. 3 is a perspective view of yet another embodiment of the present invention, illustrating another design of a double helical fastener.
FIG. 3A is a front view of the double helical fastener of FIG. 3.

In another embodiment of the surgical fastener, the fastener 110 is formed into the configuration of a double helix (See FIGS. 2–2C). By embodying a double helix, the fastener 110 has increased retentive strength as well as means to balance the fastener 110 as it is pressed into tissue. As with the helical fastener 10, the configuration of the double helical fastener 110, i.e., the pre-formed pitch and diameter, may be varied for a particular application and a barb may be employed to enhance anchoring in tissue. Moreover, the materials contemplated are the same as those for the helical fasteners. Further, the double helical fastener 110 is also longitudinally collapsible and expandable and its final pitch is dependent upon the gap 112 existing between the most distal coils 114, 115 of the fastener 110 and their adjacent coils.

Regarding the proximal 118 and distal 120 ends of the double helical fastener 110, they comprise structure to drive the fastener into tissue as well as tissue piercing structures. The proximal end 118 has a connector bar 122 sectioning the diameter of the fastener that connects one helical coil to another and functions to receive and transmit longitudinal forces. The distal end 120 terminates with two points 124, 125 for piercing and facilitating the implantation of the fastener 110 into tissue.

As may be appreciated by comparing FIGS. 2–2D with FIGS. 3–3D, it is contemplated that the double helical fastener 110 have a full turn design (FIGS. 2–2D) as well as a half turn design (FIGS. 3–3D). It is to be understood, however, that the designs having more than one turn and having other increments of turns are contemplated. It is the applicator that will determine the required number of turns for a specific fastener 110.

Figures 3B, 3C, 4:
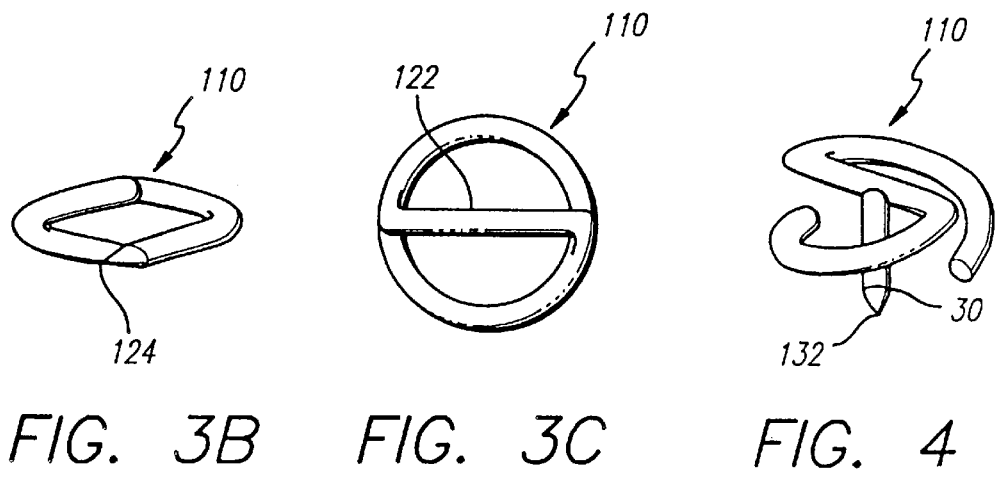
FIG. 3B is a side view of the double helical fastener of FIG. 3.
FIG. 3C is a top view of the double helical fastener of FIG. 3.
FIG. 4 is a perspective view of the present invention, illustrating a helical fastener with a central post.

In yet another embodiment of the surgical fastener, as shown in FIG. 4, the double helical fastener 110 is provided with a pivot post 130 having a pointed terminal end 132. The pivot post 130 of this embodiment operates to provide the fastener 110 with a stabilizing element so that, as the fastener 110 is being turned, the helical coils cooperatively enter the tissue.

The applicator 12 (FIG. 5) comprises a proximal portion 28 having a handle 30 and an actuator 32 and a cooperating elongated distal portion or cannula 34 housing a plurality of fasteners. In general, through the manipulation of the actuator 32, the fasteners are ejected, one by one, out of a distal portion 34 and into body tissue. The applicator 12, hereinafter described in more detail, is equally proficient in driving each of the embodiments of fasteners set forth above into tissue.

Figures 6, 6A:
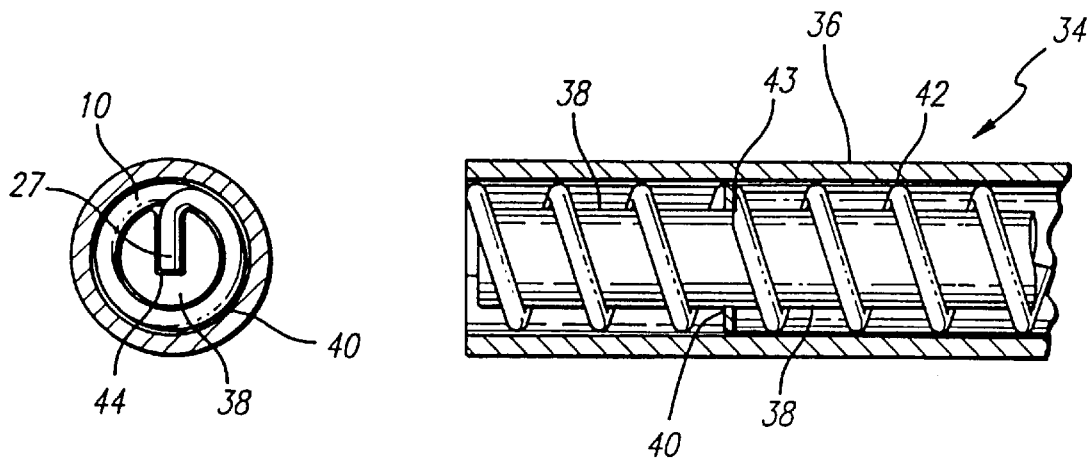
FIG. 6 is a schematic cross-sectional side view of a terminal end of the applicator.
FIG. 6A is a schematic cross-sectional end view of a terminal end of the applicator.

In more detail (see FIGS. 6 and 6A), the distal portion 34 comprises an outer tube 36 housing a rotator 38, a lock/clip indicator 40 and a load spring 42. Extending longitudinally along the rotator 38 is a groove 44 which operates to receive the most proximal coil sectioning the fastener. Although FIG. 6 shows only a single fastener (having a single helical design) retained by the rotator 38, it is to be appreciated that the rotator 38 may receive a plurality of fasteners (having a single or double helical design), wherein each fastener has its last coil positioned within the rotator groove 44. Moreover, although not depicted in FIG. 3, it is also contemplated that rather than embodying a groove, the rotator 38 has a cross-sectional profile approximately a "D", wherein the flat portion operates to engage the coil sectioning the fasteners. Irrespective of the configuration of the rotator, however, the rotator is to embody structure functioning to engage a plurality of fasteners and to facilitate turning them into tissue.

It is also to be appreciated that load spring 42 applies a force through the lock clip indicator 40 to bias the plurality of fasteners distally. The lock clip/indicator 40 may comprise a simple washer sized and shaped to engage the fasteners and rotator 38 as well as to receive forces from the load spring 42. Additionally, lock/clip indicator 40 serves as a jam stop to prevent further actuation by rotator 38 upon discharge of all fasteners by mating with, or abutting against, structure comprising the terminal end 50 and preventing further rotation. Lock/indicator 40 can be made of a color (or shape) to serve as an empty indicator notifying the user that no more fasteners are available. Other embodiments of the indicator 40 may be utilized as long as they function to transmit forces to bias the fasteners distally. The load spring 42 is to be retained within the outer tube 36 and to have physical characteristics such that sufficient forces may be applied through a front end 43 to a last remaining fastener contained within the applicator 12. A back end (not shown) of the load spring 42 may be placed against any stationery structure within the outer tube 36, thereby providing a foundation against which the spring 42 may be compressed. In a preferred embodiment, the load spring 42 extends substantially the length of the distal portion 34.

Figure 7A:
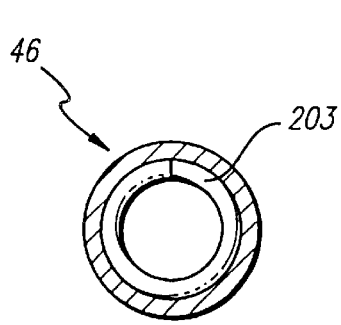
FIG. 7A is a schematic cross-sectional end view of the preferred embodiment of the terminal end of the application shown in FIG. 7.
Figure 7:
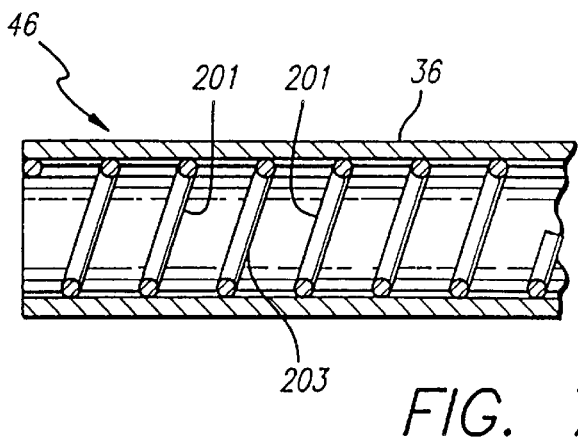
FIG. 7 is a schematic cross-sectional view of the terminal end of the applicator, illustrating the preferred embodiment of the terminal end.

In the preferred embodiment (FIGS. 7 and 7A), the outer tube 36 is configured with a thread form 201 comprising an interlock spring 203 fixedly retained within the outer tube 36 and extending substantially the length thereof. The interlock spring 203 may be fixedly retained within the outer tube 36 by ensuring a tight interference between the parts or the interlock spring may be spot welded or equivalently bonded within the outer tube. The thread form 201 operates to guide the fasteners through the distal portion 34 and to eject them from the applicator 12.

Figure 8A:
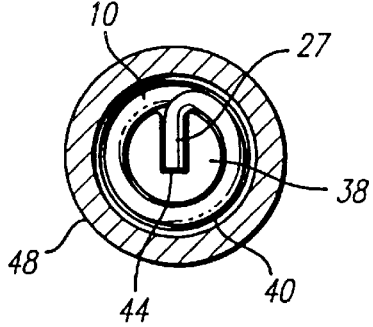
FIG. 8A is a schematic cross-sectional end view of the embodiment of the terminal end of the applicator shown in FIG. 8.
Figure 8:
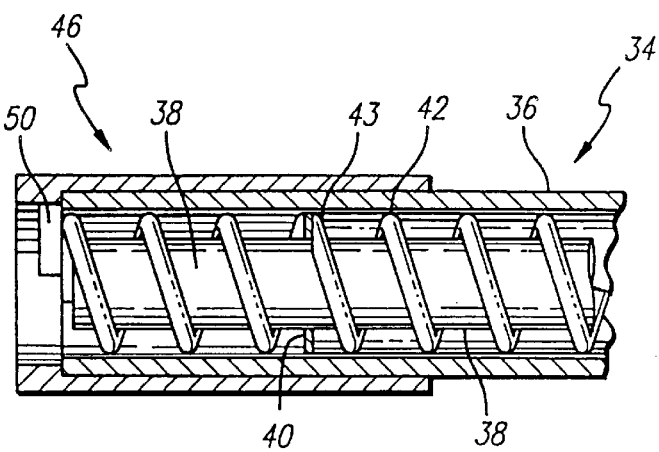
FIG. 8 is a schematic cross-sectional view of the terminal end of the applicator, illustrating another embodiment of the terminal end.

In another embodiment of the applicator 12 (FIGS. 8 and 8A), attached at a terminal end 46 of the distal portion 34 may be a nose piece 48. The nose piece 48 may further comprise a protrusion 50 extending perpendicularly and towards a longitudinal axis 52 of the distal portion 34. This nose piece protrusion 50 also functions to engage the surgical fasteners and to force them from the terminal end 46 of the distal portion 34 as well as engaging lock/clip indicator 40 as described above.

Figure 9:
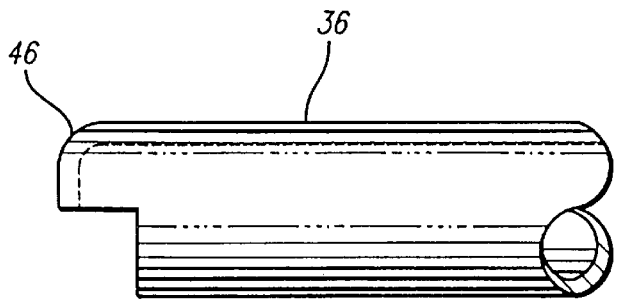
FIG. 9 is a schematic cross-sectional view of the terminal end of the applicator, illustrating yet another embodiment of the terminal end.
Figure 9A:
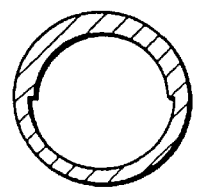
FIG. 9A is a schematic cross-sectional end view of the embodiment of the terminal end of the applicator shown in FIG. 9.
Figures 12, 12A:
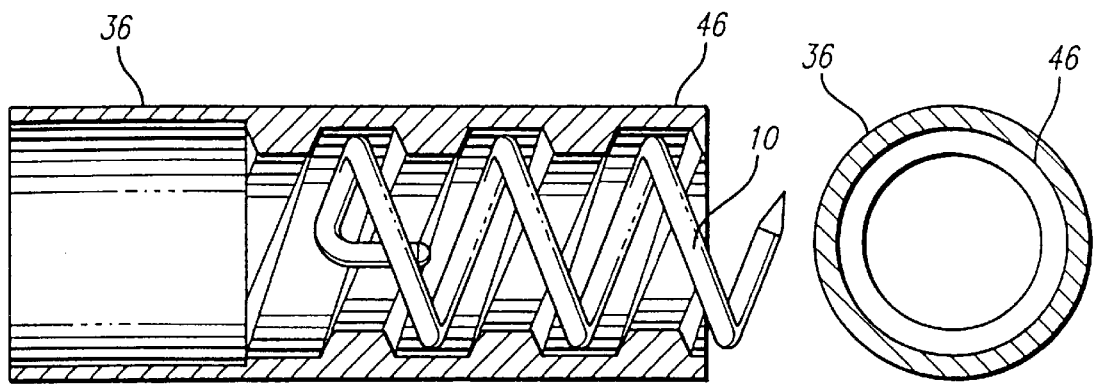
FIG. 12 is a schematic cross-sectional view of the terminal end of the applicator, illustrating a further embodiment of the terminal end.
FIG. 12A is a schematic cross-sectional end view of the embodiment of the terminal end of the applicator shown in FIG. 12.
Figure 13:
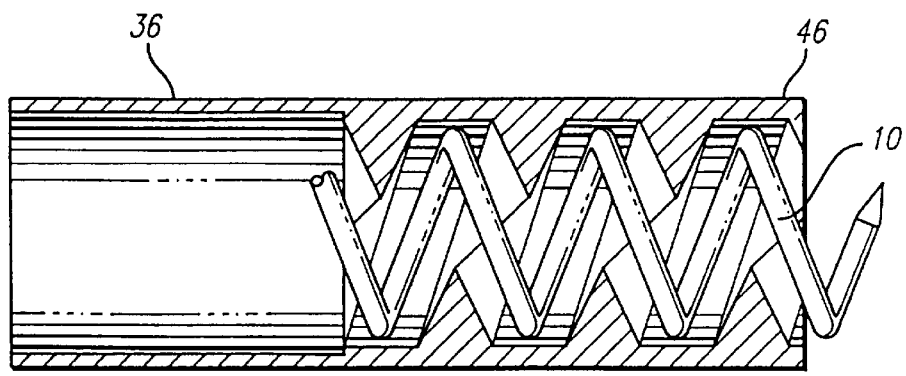
FIG. 13 is a schematic cross-sectional view of the terminal end of the applicator, illustrating a still further embodiment of the terminal end.
Figure 14:
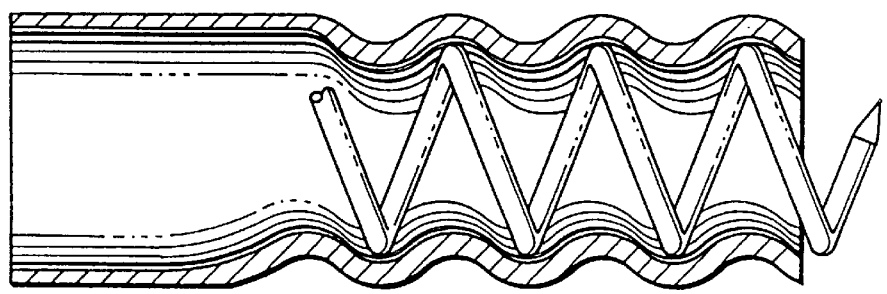
FIG. 14 is a schematic cross-sectional view of the terminal end of the applicator, illustrating still yet another embodiment of the terminal end.

In other embodiments of the applicator 12, the distal portion embodies other structure or thread forms functioning to engage the surgical fasteners and guide them out of the applicator and into tissue (See FIGS. 9–14). In FIGS. 9 and 9A, the outer tube 36 is rolled at its terminal end 46 and a 180° portion of the rolled terminal end is cut away. The remaining rolled portion engages the fastener while the portion cut away provides an exit for the fasteners. The embodiment depicted in FIGS. 10 and 10A is similar to that of FIGS. 9 and 9A, the difference being that instead of removing a portion of the rolled terminal end 46, it is stamped or deformed to thereby provide an exit. FIGS. 11 and 11A show yet another embodiment, wherein two longitudinally spaced apart stabilizing points 301, 302 are formed 180° from each other within the outer tube. These stabilizing points also operate to engage the fastener and guide it into tissue. Turning to FIGS. 12, 12A, 13 and 14, they each comprise a terminal end 46 formed with threads which operate to engage and eject a fastener. In FIGS. 12 and 12A are depicted threads machined or formed solely within the inside of the outer tube. FIG. 13 shows an internally threaded sleeve attached to the outside of the terminal end 46 of the outer tube 36. FIG. 14 illustrates an applicator 12 provided with a terminal end 46 deformed so as to have internal and external threaded structures. Irrespective of the design chosen for the terminal end of the applicator, however, each of the designs are effective with a relatively small overall outer diameter, i.e., on the order of 5 mm.

In order to eject surgical fasteners from the distal portion 34, the actuator 32 functions to turn the rotator 38. As the rotator turns, the distal end 22 of a fastener is threaded out of the terminal end 46 of the applicator 12 (see FIG. 5).

In the preferred embodiment of the proximal portion 28 of the applicator 12 (See FIG. 5), a lever 54 is pivotally connected about a midpoint 56 to the handle 30. A first end 58 of the lever 54 is to be configured for gripping by hand. A second end 60 of the lever is to be adapted to pivotally engage a nut driver 62.

The nut driver 62 of the applicator 12 travels upon a high helix lead screw 64 which is rotatably mounted within the proximal portion 28. In the preferred embodiment, a longitudinal axis of the high helix lead screw 64 is coaxial with the longitudinal axis 52 extending through the distal portion 34 of the applicator 12. Upon manipulation of the lever 54, the nut driver 62 travels along the lead screw 64 causing it to rotate through a connection of the lead screw 64 to the rotator 38, the action of the lead screw causes the rotator to rotate. The lead screw 64 may be connected to the rotator 38 by any conventional means. For instance, the lead screw 64 can have an internal bore receiving and engaging an end of the rotator 38. Further, the length of travel of the nut driver 62 along the lead screw 64 is chosen such that it causes the rotator to rotate a predetermined number of times so that a single helical fastener 10 is ejected from the applicator 12.

Additionally, in the preferred embodiment, the lever further comprises a midsection extension 66. Pivotally attached to the midsection extension 66 of the lever 54 is contemplated to be a spring loaded pawl 68 adapted to releasably engage gear teeth 70 formed in the interior of the handle 30. Spring loaded pawl 68 is configured to prohibit the lever 54 from backstroking until it has been completely depressed. Upon complete depression of the lever 54, the pawl 68 clears the gear teeth 70 and the spring biasing the pawl 68 rotates the pawl 68 away from the teeth 70, thereby allowing the lever 54 to return to its undepressed condition.

In operation, upon complete depression of the lever 54, the nut driver 62 travels a pre-determined distance along the lead screw 64, causing the rotator 38 to rotate a predetermined number of revolutions corresponding to a number of turns of a particular helical fastener 10. As the rotator 38 rotates, the fasteners retained by the rotator also rotate and the coils of the most distal fastener are threaded out of the terminal end 46 of the applicator 12 and into tissue. Moreover, where the lever 54 is only partially depressed, the spring loaded pawl 68 operates to hold the lever 54 stationery and will continue to function to hold the lever 54 stationery until the lever 54 has been completely depressed. In this way, the delivery of fasteners into body tissue is controlled so that only a single fastener may be completely ejected out of the applicator 12 and pressed into body tissue at a time.

In the preferred embodiment, the proximal portion 28 is fabricated to have a reusable handle that can be re-sterilized, and the distal portion is made disposable. Thus, upon discharge of all the fasteners 10 from distal portion 34, the distal portion would be discarded and replaced. The handle could be reused up to a limited number of procedures.

Figure 15:
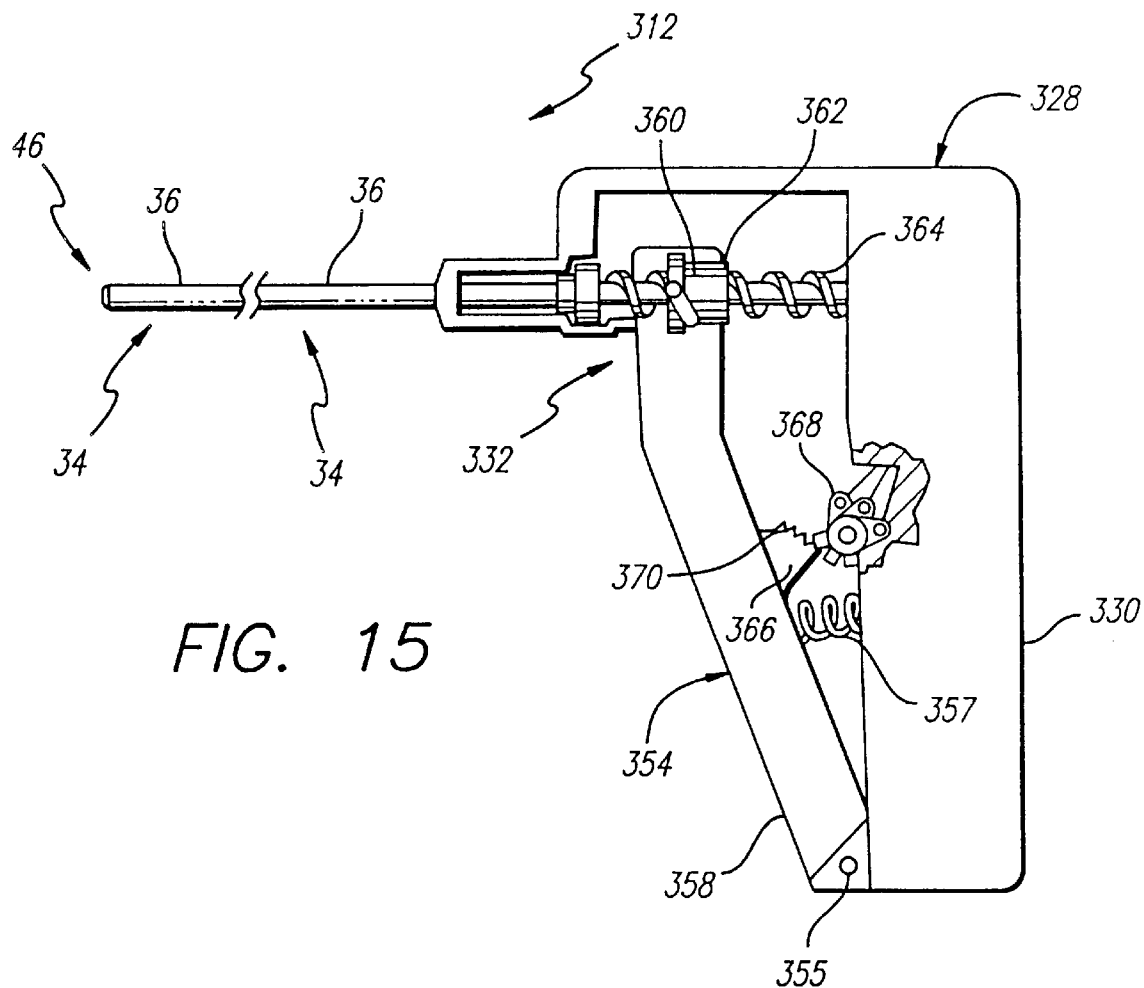
FIG. 15 is a schematic cross-sectional view of another applicator of the present invention, illustrating a side view of the applicator.

In another embodiment of the proximal portion 328, of the applicator 312 (FIG. 15), a lever 354 is pivotally connected at a first end 355 to the handle 330 and biased to its undepressed position by a spring 357. The mid-section 358 of the lower 354 is configured for gripping by hand. A second end 360 of the lever is to be adapted to pivotally engage a nut drive 362.

The nut driver 362 of the applicator 312 travels along a high helix lead-screw 364 which is rotatably mounted within the proximal portion 328. Upon manipulation of the lever 354, the nut driver travels along the lead screw 364 causing it to rotate and, through a clutch assembly or a releasable connection of the lead screw 364 to the rotator 38, the action of the lead screw causes the rotator to rotate.

Further, the lever 354, has a mid-section extension 366 that cooperates with a spring biased latch pawl mechanism 368 fixed to the handle adapted to releasably engage teeth 370 formed on the mid-section extension 366. The spring biased latch pawl is configured to prohibit the lever 354 from backstroking until it has been completely depressed. Upon complete depression of the lever 354, the latch pawl 368 clears the mid-section teeth 370 and the spring biased latch pawl 368 rotates away from the teeth, thereby allowing the lever 354 to return to its undepressed condition.

As stated, there is a releasable connection between the lead screw 364 and the rotator. The releasable connection provides the applicator with means to disengage the distal portion of the applicator from the proximal portion. In this way, the proximal portion can be re-used with various different designs of the proximal portion. Further, while the lever 354 is being depressed, the clutch assembly or releasable connection functions to transfer the rotation of the lead screw 364 to the rotator 38, thereby causing the rotator to rotate. Additionally, upon complete depression of the lever, the clutch assembly operates to allow relative motion of the lead screw 364 and the rotator.

Figure 16:
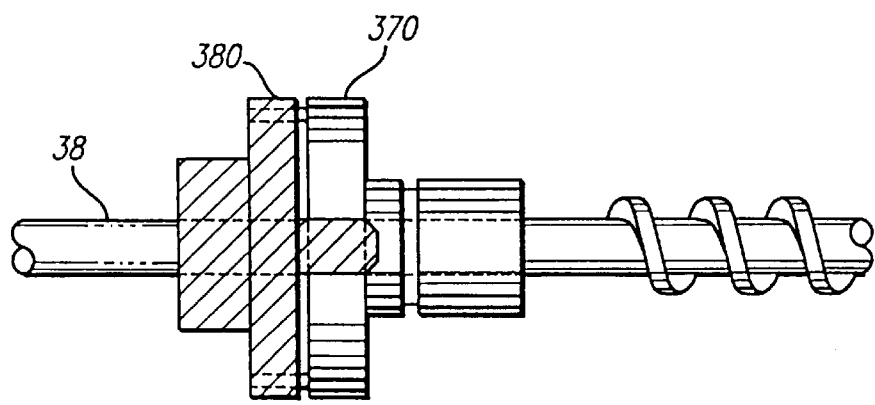
FIG. 16 is a schematic partial cross-sectional view of a releasable connection between the lead screw and rotator.
Figure 16A:
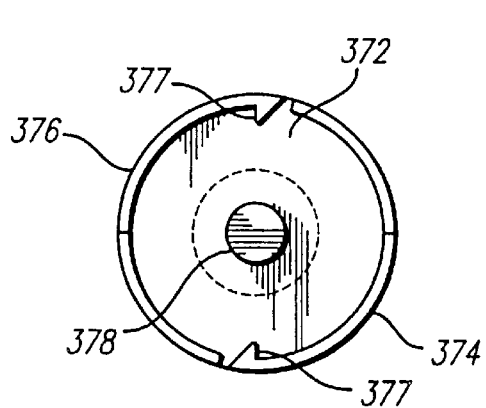
FIG. 16A is schematic representation of a distal end of the lead screw, illustrating an end view of the lead screw.
Figure 16B:
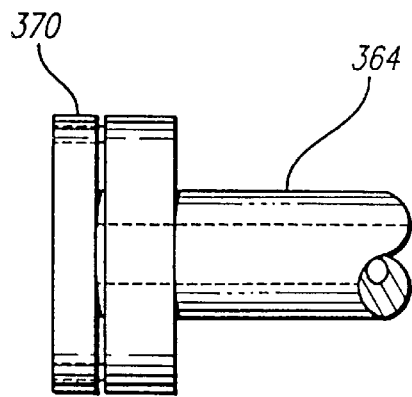
FIG. 16B is a schematic representation of the distal end of the lead screw, illustrating a side view of the lead screw depicted in FIG. 16.
Figure 16C:
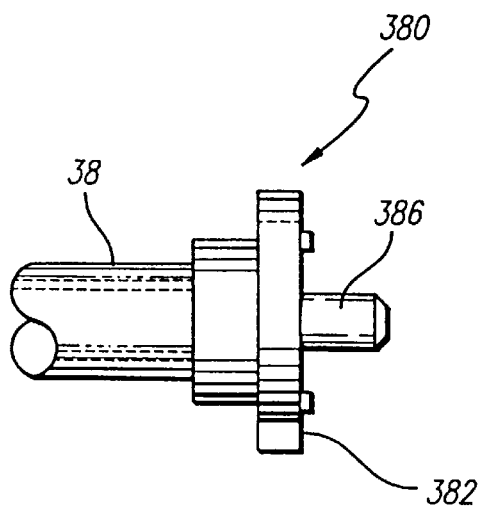
FIG. 16C is a schematic representation of the proximal end of the rotator, illustrating a side view of the rotator.
Figure 16D:
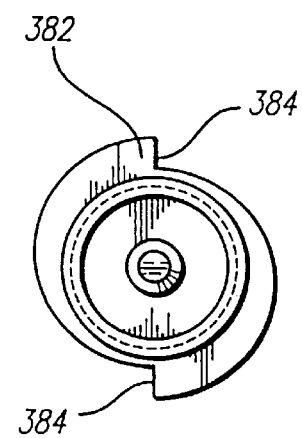
FIG. 16D is a schematic representation of the proximal end of the rotator, illustrating an end view of the rotator depicted in FIG. 16B.

One such releasable connection contemplated is a conventional ratchet mechanism. As shown in FIGS. 16–16D, the distal end 370 of the lead screw 364 has a connecting surface 372 equipped with leaf springs 374, 376 each having an engaging face 377 and an internal bore 378 existing coaxially with a longitudinal axis of the lead screw. The proximal end 380 of the rotator 38 has a cooperating connecting surface 382 having ridges 384 for releasable engagement with the leaf springs 374, 376 and an extension 386 adapted to fit within the internal bore of the lead screw connecting surface. As may be appreciated from the FIGS., as the lead screw turns so that the ridges 384 contact the engaging faces 377 of the leaf springs 374, 376, the rotation of the lead screw 364 will cause the rotator 38 to likewise rotate. Where the lead screw is turned in the opposite direction, the ridges 384 will not engage the engaging face of the leaf springs and the motion of the lead screw 384 will not be transferred to the rotator 38.

In this embodiment, upon complete depression of the lever 354, the nut driver 362 travels a pre-determined distance along the lead screw 364, causing the rotator 38 to rotate a pre-determined number of revolutions. As the rotator 38 rotates, the fasteners retained by the rotator also rotate and the coils of the most distal fasteners are threaded out of the applicator and into the tissue. At this point, the latch pawl mechanism 368 disengages from the teeth 370 and the lever 354 is returned to its undepressed position by spring 357. As with the previous embodiment of the proximal portion 28, the proximal portion of this embodiment functions to allow only a single fastener to be completely ejected from the applicator and be pressed into body tissue at a time.

In other embodiments, means to cause the rotator to rotate may comprise a single knob connected to a rotator which can be turned by hand. Additionally, the revolving means may include a rack and gear structure or a set of beveled gears. Further, instead of comprising a groove, the rotator may be internally threaded, wherein the threaded portions function to house as well as advance the helical fasteners 10. Irrespective of the means or structure employed, however, it is contemplated that the number of revolutions of the rotator be set to a pre-determined parameter so that the delivery of helical fasteners to tissue may be controlled.

From the foregoing, it will be appreciated that the helical fastener in applicator of the present invention functions to securely attach a fastener with high retentive surface area to tissue from one direction through the utilization of an applicator having a simple design. It is also to be appreciated that the present invention may be utilized in a number of applications including ligating tissue, hernia mesh repair, bladder neck suspension, and in conjunction with implant drug delivery systems or procedures involving positioning of surgical or implantable devices in patient.

While several particular forms of the invention have been illustrated and described, it will also be apparent that various modifications can be made without departing from the spirit and scope of the invention.

Thus, it should be understood that various changes in form, detail and application of the present invention may be made without departing from the spirit and scope of this invention.

What is claimed is:

1. A system for applying fasteners to body tissue, comprising:

a plurality of fasteners, each having a helical configuration;

an applicator for applying said fasteners to body tissue, said applicator having a distal portion and a proximal portion;

said distal portion having an elongate outer tube, a connecting end and a terminal end, said terminal end having internal threads;

said proximal portion having a handle and an actuator, said proximal portion attached to said connecting end of said distal portion; and said plurality of fasteners being configured within said distal portion and advanced through said threads upon manipulation of said actuator.

2. The system of claim 1, wherein said threads are formed within interior walls of said outer tube.

3. The system of claim 1, wherein said distal portion further comprises a sleeve attached to said outer tube, said sleeve defining said internal threads.

4. The system of claim 1, wherein said threads are formed by deforming said terminal end of said outer tube.

5. The system of claim 1, wherein each said fastener defines a plurality of adjacent coils, at least one of said fasteners having said adjacent coils configured within threads of said terminal end.

6. The system of claim 1, wherein said threads guide said fasteners out of said distal portion.

7. The system of claim 1, said applicator further comprising a rotator for receiving said plurality of fasteners and for cooperating with said actuator, wherein upon rotation of said rotator, said fasteners advance through said distal portion and said threads.

8. The system of claim 1, wherein upon manipulation of said actuator, said fasteners are rotated through said threads.

9. The system of claim 1, wherein said threads define the pitch of said fasteners as said fasteners exit said distal portion.

\* \* \* \* \*